US010017713B2

(12) United States Patent
Lamanna et al.

(10) Patent No.: US 10,017,713 B2
(45) Date of Patent: Jul. 10, 2018

(54) FLUORINATED SURFACTANT CONTAINING COMPOSITIONS

(71) Applicant: 3M INNOVATIVE PROPERTIES COMPANY, St. Paul, MN (US)

(72) Inventors: William M. Lamanna, Stillwater, MN (US); Patricia M. Savu, Maplewood, MN (US); Jason M. Kehren, Stillwater, MN (US); Liping Claryn Ng, Bahru (SG); Namiko Ikegaya, Tokya (JP)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/508,939

(22) PCT Filed: Sep. 10, 2015

(86) PCT No.: PCT/US2015/049300
§ 371 (c)(1),
(2) Date: Mar. 6, 2017

(87) PCT Pub. No.: WO2016/040551
PCT Pub. Date: Mar. 17, 2016

(65) Prior Publication Data
US 2017/0283740 A1  Oct. 5, 2017

Related U.S. Application Data

(60) Provisional application No. 62/048,836, filed on Sep. 11, 2014.

(51) Int. Cl.
| C11D 3/43 | (2006.01) |
| C11D 1/00 | (2006.01) |
| B08B 3/08 | (2006.01) |
| B08B 3/02 | (2006.01) |
| B08B 5/02 | (2006.01) |
| C07C 311/09 | (2006.01) |

(52) U.S. Cl.
CPC ............. *C11D 1/002* (2013.01); *B08B 3/02* (2013.01); *B08B 3/08* (2013.01); *B08B 5/02* (2013.01); *C07C 311/09* (2013.01); *C11D 1/004* (2013.01); *C11D 3/43* (2013.01)

(58) Field of Classification Search
CPC ....... C11D 1/004; C11D 11/0048; C11D 1/83; C11D 3/3947; C11D 3/43
USPC .................................................. 510/175, 176
See application file for complete search history.

(56) References Cited

U.S. PATENT DOCUMENTS

| 3,734,962 A | 5/1973 | Niederprum |
| 3,929,720 A | 12/1975 | Rosendahl |
| 6,297,308 B1 | 10/2001 | Jariwala |
| 6,376,452 B1 | 4/2002 | Flynn |
| 6,890,452 B2 | 5/2005 | Parent |
| 7,169,323 B2 | 1/2007 | Parent |
| 7,662,896 B2 | 2/2010 | Savu |
| 9,454,082 B2* | 9/2016 | Lamanna ................. C08F 14/18 |
| 9,725,683 B2* | 8/2017 | Lamanna ............. C11D 11/0047 |
| 2007/0072985 A1 | 3/2007 | Hintzer |
| 2010/0155657 A1 | 6/2010 | Savu |
| 2010/0155658 A1 | 6/2010 | Sauer |
| 2010/0160458 A1* | 6/2010 | Savu ....................... C11D 1/004 516/9 |
| 2010/0320416 A1* | 12/2010 | Savu ....................... C11D 1/004 252/79.3 |
| 2014/0154632 A1 | 6/2014 | Kehren |
| 2015/0370171 A1* | 12/2015 | Lamanna ................. C08F 14/18 430/331 |
| 2016/0376533 A1* | 12/2016 | Lamanna ................. C08F 14/18 510/176 |
| 2017/0114308 A1* | 4/2017 | Lamanna ............. C11D 11/0047 |
| 2017/0283365 A1* | 10/2017 | Lamanna .............. C07C 217/26 |

FOREIGN PATENT DOCUMENTS

| JP | 2005223184 | 8/2005 |
| WO | WO 2001-27235 | 4/2001 |
| WO | WO 2013-162705 | 10/2013 |
| WO | WO 2014-120405 | 8/2014 |

OTHER PUBLICATIONS

Ellis, "Cleaning and Contamination of Electronics Components and Assemblies", Electrochemical Publications Limited, 1986, pp. 182-195.
Mouser, "Organic Solvent Cleaning: Solvent and Vapor Phase Equipment Overview", Handbook for Critical Cleaning: Cleaning Agents and Systems, 2011, pp. 363-372.
Owens, "Hydrofluoroethers", Handbook for Critical Cleaning: Cleaning Agents and Systems, 2011, pp. 115-129.
International Search Report for PCT International Application No. PCT/US2015/49300, dated Jan. 15, 2016, 3 pages.

* cited by examiner

*Primary Examiner* — Gregory Webb
(74) *Attorney, Agent, or Firm* — Adam Bramwell

(57) ABSTRACT

A composition includes a fluorinated or perfluorinated organic solvent, and a fluorinated surfactant of the general formula (1): [Formula should be inserted here] Rf is a perfluoroalkyl group having 1-6 carbon atoms. Each occurrence of $R_1$ and $R_2$ is independently H or $CH_3$, n is 1-3, and x is 1-3.

$$RfSO_2-N\begin{matrix}(CH_2-CHO)_n-H \\ | \\ R_1 \\ \\ (CH_2-CHO)_x-H \\ | \\ R_2\end{matrix} \quad (1)$$

14 Claims, No Drawings

FLUORINATED SURFACTANT CONTAINING COMPOSITIONS

CROSS REFERENCE TO RELATED APPLICATIONS

This application is a national stage filing under 35 U.S.C. 371 of PCT/US2015/049300, filed Sep. 10, 2015, which claims the benefit of U.S. Application No. 62/048,836, filed Sep. 11, 2014, the disclosure of which is incorporated by reference in its/their entirety herein.

FIELD

The present disclosure relates to working fluids that can be useful for cleaning or removing contaminants, in particular to compositions including a fluorochemical surfactant and an organic solvent.

BACKGROUND

Various fluorochemical surfactants for use in cleaning compositions are described in, for example, U.S. Pat. No. 6,376,452, JP Publication 2005223184, U.S. Pat. No. 6,297,308, and PCT Publication WO 2014/120405.

SUMMARY

In some embodiments, a composition is provided. The composition includes a fluorinated or perfluorinated organic solvent, and a fluorinated surfactant of the general formula (1):

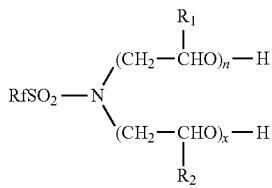

Rf is a perfluoroalkyl group having 1-6 carbon atoms. Each occurrence of $R_1$ and $R_2$ is independently H or $CH_3$; n is 1-3, and x is 1-3.

In some embodiments, a process for removing contaminants from a substrate is provided. The process includes contacting the substrate with the above-described composition.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

Hydrofluoroether fluids are widely used in solvent precision cleaning applications due, at least in part, to their good cleaning performance, zero ozone depletion potential, low global warming potential, and low toxicity. Also, because hydrofluoroether fluids are often nonflammable, they can be used safely in a wide variety of applications.

Some hydrofluoroethers can be used "neat" (without cosolvent or surfactant additives) to remove light contamination such as particles, hydrocarbon and silicone oils. These neat solvents function effectively in the removal of weakly bound particulates and highly soluble contaminants from components and final assemblies. Mixtures of hydrofluoroethers with small amounts of alcohol cosolvents typically provide increased solvency and improved cleaning performance (for removal of oils and greases) and particle removal/reattachment efficiencies while still maintaining sufficient materials compatibility with typical electronic and optical component substrates. However, even these higher performance cleaning fluids can be inadequate in cleaning tightly bound particles and less soluble residues from the most heavily soiled parts. For example, cleaning and contaminant removal can be especially challenging for complementary metal-oxide-semiconductor (CMOS) parts with relatively high pixel densities. For such parts, any particles, organic residues, or water stains resulting from wafer dicing, die-attach, and assembly processes can cause a significant adverse impact on the quality of the output image. Thus, an improved cleaning fluid formulation that can provide better cleaning performance and improved particle removal and/or particle reattachment efficiencies for the most heavily soiled and challenging parts may be desirable.

Various surfactants have been discussed as useful additives for hydrofluoroether-based cleaning compositions. However, such surfactants have been found, in large part, to be undesirable due to their toxicity, tendency to bioaccumulate, poor solubility, high cost, and/or inadequate cleaning performance.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, a "hydrofluoroether" means an organic ether compound containing both H and F atoms bound to carbon.

As used herein, a "segregated hydrofluoroether" means a hydrofluoroether having a perfluorinated segment (such as alkyl or alkylene segments) linked via an ether oxygen to a non-fluorinated segment.

As used herein, "substituted" (in reference to a group or moiety) means that at least one carbon-bonded hydrogen atom is replaced with a halogen atom. Halogen atoms may include F, Cl, Br, and I.

As used herein, "fluorinated surfactant" means a fluorine containing compound having at least one liphophilic group or portion and at least one hydrophilic group or portion.

As used herein, "fluorinated ionic surfactant" means a fluorinated surfactant that is capable of ionizing in solution, including protic surfactants that include acidic N—H groups.

As used herein, "fluorinated organic solvent" is used as generally accepted in the art of organofluorine chemistry, and includes, but is not restricted to, fluorinated organic compounds generally taking the form of a carbon backbone substituted with fluorine atoms and optionally substituted with hydrogen and/or chlorine or other halogen atoms; the carbon backbone can be interrupted by heteroatoms such as divalent oxygen, trivalent nitrogen, sulfur, etc. Examples of fluorinated solvents include hydrofluorocarbons (HFCs), perfluorocarbons (PFCs), hydrofluoroethers (HFEs), hydrohalofluoroethers (HEFEs) such as hydrochlorofluoroethers (HCFEs), hydrofluoroolefins (HFOs), hydrochlorofluoroolefins (HCFOs), chlorofluorocarbons (CFCs), and hydrochlorofluorocarbons (HCFCs), alone or as a mixture.

As used herein, "non-flammable", as it relates to organic solvents and organic solvent mixtures (with cosolvents), means that the solvent has a closed cup flash point above 100 degrees Fahrenheit according to ASTM D-3278-96 e-1. As a general rule, for a fluorinated organic solvent containing only fluorine, hydrogen, and carbon atoms (e.g., an HFC), and optional divalent oxygen atoms (e.g., an HFE) to be non-flammable, the relationship between the number of fluorine, hydrogen, and carbon atoms is such that the number of fluorine atoms divided by the number of combined hydrogen atoms and carbon-carbon bonds is greater than or equal to about 0.8 according to the following equation: # of F atoms/(#H atoms+#C—C bonds)≥0.8.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to compositions useful for removing contaminants from (or cleaning) a substrate. Generally, the compositions may include a fluorinated surfactant and an organic solvent.

In various embodiments, the fluorinated surfactant may include one or more $C_nF_{2n+1}SO_2N$-based fluorinated surfactants. For example, the fluorinated surfactant may include one or more non-ionic surfactants represented by the general formula (1):

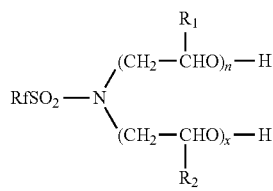

where Rf is a perfluoroalkyl group having 1-6, 2-4, or 4 carbon atoms; each occurrence of $R_1$ and $R_2$ is independently H or $CH_3$; n is 1-3; and x is 1-3. In some embodiments, the molecular weight of the fluorinated surfactants may be less than 450 or less than 500 atomic mass units.

In some embodiments, the surfactant may be present in the composition in an amount sufficient to promote soil, particle, or contaminant removal. The surfactants may be present in the composition in an amount of no more than 5 wt. %, no more than 1 wt. %, no more than 0.5 wt. %, no more than 0.1 wt. %, no more than 0.05 wt. %, no more than 0.01 wt. %, between 0.01 and 1 wt. %, between 0.03 and 0.5 wt. %, or between 0.05 and 0.3 wt. %, based on the total weight of the composition.

In some embodiments, in addition to the above-described fluorinated surfactant, the compositions of the present disclosure may include a second surfactant (or synergist). The second surfactant may also be a fluorinated surfactant. In some embodiments, the second surfactant may include a fluorinated ionic surfactant. The fluorinated ionic surfactant may be represented by general formula (2):

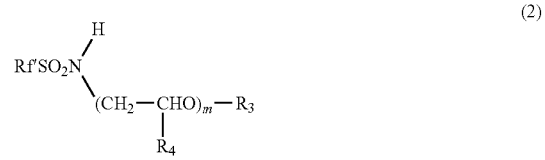

where m is 1-3, each occurrence of $R_4$ is independently H or $CH_3$, $R_3$ is H or an alkyl group, and Rf' is a is a perfluoroalkyl group having 1-6, 2-4, or 4 carbon atoms. In some embodiments, $R_3$ is H. The second surfactant may be present in the composition in an amount of no more than 5 wt. %, no more than 1 wt. %, no more than 0.5 wt. %, no more than 0.1 wt. %, no more than 0.05 wt. %, no more than 0.01 wt. %, between 0.01 and 1.0 wt. %, between 0.03 and 0.5 wt. %, or between 0.05 and 0.3 wt. %, based on the total weight of the composition.

In some embodiments, the organic solvent may include a primary organic solvent (i.e., a solvent or combination of solvents that are present in an amount of greater than 50 wt. %, based on the total weight of the composition) and optionally one or more co-solvents. In some embodiments, the primary organic solvent may include a fluorinated or perfluorinated organic solvent. In some embodiments, the fluorinated or perfluorinated primary organic solvent may include a non-flammable fluorinated or perfluorinated organic solvent. In some embodiments, the non-flammable fluorinated or perfluorinated primary organic solvent may include hydrofluoroethers (HFEs), hydrofluorocarbons (HFCs), hydrofluoroolefins (HFOs), hydrochlorofluoroolefins (HCFOs), fluoroketones, perfluoroketones, or combinations thereof. In some embodiments, the non-flammable fluorinated or perfluorinated primary organic solvent may include (or consist essentially of) a hydrofluoroether. In some embodiments, the hydrofluoroether may include (or consist essentially of) a segregated hydrofluoroether. Other suitable hydrofluoroether solvents may include those described in U.S. Pat. Nos. 6,376,452 and 6,297,308, which are herein incorporated by reference in their entirety.

In various embodiments, the primary organic solvent(s), may be present in the composition in an amount of at least 50 wt. %, at least 75 wt. %, at least 95 wt. %, at least 99 wt. %, at least 99.5 wt. %, at least 99.9 wt. %, between 75 wt.

% and 99 wt. %, 95 and 99 wt. %, between 99 and 99.5 wt. %, or between 99.5 and 99.9 wt. %, based on the total weight of the composition.

In illustrative embodiments, the compositions of the present disclosure may additionally include one or more fluorinated, perfluorinated, or nonfluorinated co-solvents (i.e., a solvent component present at less than 50 wt. %, less than 20 wt. %, less than 5 wt. % or less than 1 wt. %) based on the total weight of the composition). Suitable co-solvents may include alcohols, ethers, alkanes, alkenes, haloalkenes, perfluorocarbons (PFCs), perfluoroolefins, perfluorinated tertiary amines, perfluoroethers, cycloalkanes, esters, ketones, aromatics, haloaromatics, siloxanes, silicones, hydrochlorocarbons, hydrochlorofluorocarbons, or combinations thereof such co-solvents can be chosen to modify or enhance the properties of a cleaning composition (e.g., solvency, flammability, boiling point, particle removal, and particle reattachment efficiency) for a particular use.

In some embodiments, the organic solvent/cosolvent mixture may be an azeotropic mixture wherein the overall solvent composition does not change significantly with evaporation.

In some embodiments, suitable alcohol co-solvents may include methanol, ethanol, n-propanol, isopropanol, t-butyl alcohol, i-butyl alcohol, n-butyl alcohol, sec-butyl alcohol, tetrahydrofurfuryl alcohol, ethylene glycol, ethylene glycol monomethylether, ethyleneglycol monoethyl ether, propylene glycol, cyclopentanol, glycerol, trifluoroethanol, tetrafluoropropanol, hexafluorobutanol, and hexafluoro-i-propanol In various embodiments, the alcohol co-solvent may be present in the composition at less than 50 wt. %, less than 30 wt. %, less than 10 wt. %, less than 5 wt. %, less than 3 wt. %, between 1 and 50 wt. %, between 1 and 30 wt. %, between 1 and 10 wt. %, between 1 and 5 wt. %, or between 1 and 3 wt % based on the total weight of the composition.

In various embodiments, the organic solvent(s), including optional cosolvents, may be present in the composition in an amount of at least 95 wt. %, at least 99 wt. %, at least 99.5 wt. %, at least 99.9 wt. %, between 95 and 99 wt. %, between 99 and 99.5 wt. %, or between 99.5 and 99.9 wt. %, based on the total weight of the composition.

In some embodiments, various additives may be included in the compositions of the present disclosure (e.g., in order to improve cleaning performance). Suitable additives may include, for example, complexing agents, water, ozone, or hydrogen peroxide. The additives may be present at less than 5 wt. %, based on the total weight of the composition.

In some embodiments, the $C_nF_{2n-1}SO_2N$-based fluorinated surfactants of the present disclosure can be prepared by deprotonating a fluorochemical sulfonamide containing at least one acidic N—H group with a base to form a fluorochemical sulfonamide anion, which can then nucleophilically attack an electrophilic reagent, as illustrated in Scheme I below. Since the protons of a fluorochemical sulfonamide are acidic due to electron withdrawal by the fluoroalkylsulfonyl group, a variety of different bases can be used to facilitate deprotonation, such as alkali metal carbonates, organic amines, or alkali metal alkoxides. The electrophilic reagent can, for example, be a polyoxyalkyl halide (where the halide is chloride or bromide or iodide), or a cyclic epoxide (like ethylene oxide or propylene oxide) or a cyclic organic carbonate reagent (like ethylene carbonate or propylene carbonate) that ring opens, with or without oligomerization. In the case of the cyclic organic carbonate reagents, $CO_2$ byproduct may be released in the course of the ring opening reaction. Scheme I below illustrates a non-limiting example of a process that may be used to append a polyethylene oxide chain to a fluorinated sulfonamide N atom. When R is H, the process of Scheme I can be repeated to append two polyethylene oxide chains to the sulfonamide N atom. However, it is to be appreciated that other routes, including those described in the Examples section of the present disclosure, may be employed.

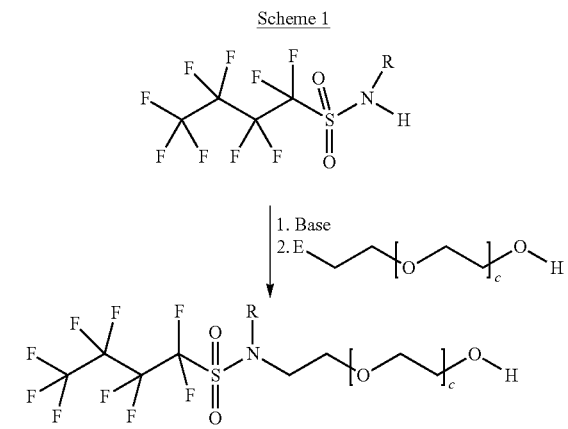

Scheme 1

The present disclosure is further directed to methods of removing contaminants from (or cleaning) a substrate using the above-described compositions. The methods may include contacting a contaminated substrate with the above-described compositions. The compositions can be used in either the gaseous or the liquid state (or both), and any of the known techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various solvent cleaning techniques are described by Barbara and Edward Kanesburg, *Handbook of Critical Cleaning: Cleaning Agents and Systems*, edited by CRC Press, pages 123-127 and 363-372 (2011); and B. N. Ellis in *Cleaning and Contamination of Electronics Components and Assemblies*, Electrochemical Publications Limited, Ayr, Scotland, pages 182-94 (1986), which are both herein incorporated by reference in their entirety.

Both organic and inorganic substrates can be cleaned by the cleaning methods of the present disclosure. Representative examples of the substrates include metals; ceramics; glass; semiconductors; polycarbonate; polystyrene; acrylonitrile-butadiene-styrene copolymer; synthetic non-woven materials; natural fibers (and fabrics derived therefrom) such as cotton, silk, fur, suede, leather, linen, and wool; synthetic fibers (and fabrics) such as polyester, rayon, acrylics, nylon, and blends thereof; fabrics comprising a blend of natural and synthetic fibers; and composites of the foregoing materials. The process may be useful in the precision cleaning of optical and electronic components, subassemblies, or devices, such as circuit boards, wafers and integrated circuit chips (including those based on Si, Ge and Si/Ge semiconductors), CMOS parts, display components, optical or magnetic media, UV or EUV photomasks (such as those used in semiconductor photolithography), as well as various medical devices.

In some embodiments, the cleaning processes of the present disclosure can be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes, particulates; and other contaminants encountered in precision, electronic, metal, and medical device cleaning can be removed. In some embodiments, the process may be used for the removal of hydrocarbon contaminants (especially, light hydrocarbon oils), fluorocarbon contaminants, and organic and inorganic particulates.

Surprisingly, it was discovered that the fluorinated surfactants of the present disclosure provide acceptable solubility in hydrofluoroether based solvents and excellent cleaning performance, despite their relatively short fluorochemical tails. Moreover, the fluorinated surfactants of the present disclosure are expected to be non-toxic and have negligible potential to bioconcentrate. Thus, these surfactants provide a sustainable alternative to known fluorochemical surfactants for use in hydrofluoroether-based cleaning compositions. The improved hydrofluoroether-based cleaning compositions of the present disclosure can facilitate improved cleaning of heavily soiled sensitive electronic and optical components (e.g., higher pixel density CMOS devices).

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Surfactant Synthesis

Synthesis 1: $C_4F_9SO_2N(H)CH_2CH(CH_3)OH$ (I, H-FBSP) and $C_4F_9SO_2N[CH_2CH(CH_3)OH]_2$ (II, FBSPP)

$C_4F_9SO_2NH_2$ (100.00 g, 0.3343 mol) (prepared as described in U.S. Pat. No. 7,169,323), $K_2CO_3$ powder (5.54 g, 0.0401 mol), and anhydrous propylene carbonate (68.26 g, 0.6687 mol) were batch charged to a 200 mL round bottom flask equipped with a Claisen adapter, water cooled condenser with nitrogen inlet line, immersion thermocouple probe, magnetic stirrer and heating mantle. The reaction mixture was gradually heated to 160° C. under nitrogen with stirring and then held at 160° C. for about 15 hours. After cooling to room temperature, an aliquot of the reaction mixture was removed and analyzed by GC in acetone. GC-FID analysis revealed the presence of about 38% $C_4F_9SO_2N(H)CH_2CH(CH_3)OH$ and 24% $C_4F_9SO_2N[CH_2CH(CH_3)OH]_2$ (mix of two diastereomers). Peak assignments were confirmed by GC-MS. To the reaction mixture was added 69.4 g of deionized water and 19.4 g of 20 wt % $H_2SO_4$(aq). After heating to 60° C. to reduce viscosity the reaction mixture was stirred vigorously to neutralize all residual base and then transferred to a separatory funnel and allowed to phase separate. The lower product phase was separated, washed with about 60 mL of additional hot water and then phase separated again. The lower product phase was isolated and then dissolved in 240 g of MTBE (methyl t-butyl ether available from Sigma-Aldrich, St Louis, Mo.) to cut viscosity and facilitate additional extractions. After filtration by gravity through fluted filter paper, the product solution in MTBE was transferred to a 1.0 L separatory funnel and extracted with three 300 mL portions of deionized (DI) water. The upper MTBE/product phase was isolated and then concentrated on a rotary evaporator at 20 Torr, 20-50° C. to remove bulk of MTBE solvent to isolate crude product.

The crude product was then fractionally distilled under vacuum (3 Torr) through a short Vigreux column to separate and isolate the two desired product fractions. Fraction #2 comprising 36.4 g of 92.1% pure $C_4F_9SO_2N(H)CH_2CH(CH_3)OH$ was collected at a head temperature of 128-133° C. Fraction #5 comprising 12.49 g of 91.7% pure $C_4F_9SO_2N[CH_2CH(CH_3)OH]_2$ (mix of two diastereomers) was collected at a head temperature of 148.0-148.5° C. The two isolated product fractions (#2 and #5) were separately dissolved in hot toluene to 20% solids, filtered hot to remove insolubles, and then allowed to cool to room temperature and recrystallize. Once recrystallization was complete, the white crystalline solids that formed were isolated by vacuum filtration, washed with toluene at room temperature (RT) and then recrystallized a second time from hot toluene at about 30% solids using a similar procedure. The isolated crystalline solids were vacuum dried at 60-65° C. for about 3 hours in a vacuum oven at about 80 mTorr to remove residual toluene and other volatiles. The final isolated yield of $C_4F_9SO_2N(H)CH_2CH(CH_3)OH$ from Fraction #2 was 27.082 g with a GC-FID purity of 98.54%. $C_4F_9SO_2N(H)CH_2CH(CH_3)OH$ was a solid with a melting point of 80.33° C. as determined by DSC.

The final isolated yield of $C_4F_9SO_2N[CH_2CH(CH_3)OH]_2$ from Fraction #5 was 8.537 g with a GC-FID purity of 99.77% (approximately 50:50 mixture of two possible diastereomers). In both cases the only observable impurity was residual toluene solvent. Both purified product samples were analyzed by $^1H$, $^{19}F$ and $^{13}C$ NMR spectroscopy to determine the identities and relative quantities of the primary isomeric components. The product isolated from distillate Fraction #2 was found to contain 98.3% $C_4F_9SO_2N(H)CH_2CH(CH_3)OH$ (major isomer) and 1.7% $C_4F_9SO_2N(H)CH(CH_3)CH_2OH$ (minor isomer). Fraction #5 was found to contain 99.2% $C_4F_9SO_2N[CH_2CH(CH_3)OH]_2$ (major isomer) and 0.8% $C_4F_9SO_2N[CH_2CH(CH_3)OH][CH(CH_3)CH_2OH]$ (minor isomer). The NMR results confirm that propylene carbonate is preferably attacked by the nucleophilic sulfonamide nitrogen at the unsubstituted, secondary —$CH_2$— carbon to form the major mono-ol and diol product isomers.

When dissolved in an organic solvent at an effective concentration, compound II (FBSPP) is expected to provide improved particle cleaning performance vs. an organic solvent that is free of surfactant. Compound I (H-FBSP) is expected to be a useful synergist, which, when combined with compound II or one or more other surfactants of the present invention and dissolved in an organic solvent at an effective concentration, will provide improved particle cleaning performance vs. an organic solvent that is free of surfactant or contains one or more surfactants of the present invention but no synergist.

Synthesis 2: $C_4F_9SO_2N(H)CH_2CH_2OCH_2CH_2OH$ (III, H-FBS(EE))

$C_4F_9SO_2NH_2$ (100.00 g, 0.3343 ml) and triethylamine (101.48 g, 1.0029 mol) were batch charged to a 500 mL, 3-necked round bottom flask equipped with a Claisen adapter, addition funnel, water cooled condenser with nitrogen inlet line, immersion thermocouple probe, mechanical stirrer and heating mantle. After heating mixture to a set point of 60° C., $ClCH_2CH_2OCH_2CH_2OH$ (53.726 g, 0.4313 mol; available from Alfa Aesar, Ward Hill, Mass.) was gradually added with stirring from addition funnel over a period of 40 minutes without significant exotherm or precipitate. Reaction temperature was increased to 95° C. and held for 17 hours resulting in formation of significant white precipitate ($Et_3NH^+Cl^-$). GC analysis of an aliquot of the reaction mixture indicated that the reaction had proceeded to only 36.5% conversion, so an additional 10.00 g of $ClCH_2CH_2OCH_2CH_2OH$ was charged to the reaction mixture via syringe and the mixture was allowed to react at 95° C. for an additional 66 hours with stirring. After cooling to room temperature, an aliquot of the reaction mixture was removed for GC-FID analysis, which revealed 23.1% unreacted $C_4F_9SO_2NH_2$, 52.2% $C_4F_9SO_2N(H)CH_2CH_2OCH_2CH_2OH$ (desired product) and 24.8% of the corresponding diol, $C_4F_9SO_2N[CH_2CH_2OCH_2CH_2OH]_2$. To the cooled reaction mixture was added 69 g deionized water and 99.4 g of 20% $H_2SO_4$(aq) with stirring. The resulting mixture was transferred to a 1.0 L reparatory funnel and extracted with 239 g MTBE. The lower aqueous phase was separated and drained and the remaining MTBE/product phase was washed with 300 mL of deionized water. A stable emulsion formed, which was broken by adding a small amount of concentrated aqueous NaCl and 150 mL of 42.5% phosphoric acid. After this first wash, the lower aqueous phase was drained and the remaining MTBE phase was washed two more times with a mixture of 300 mL of water and 150 ml of 42.5% phosphoric acid. A stable emulsion was formed again during the third wash, so entire contents of separatory funnel were drained into a beaker and the MTBE was allowed to evaporate. This resulted in clean phase separation of the product (lower phase) from the aqueous acid (upper phase). The lower product phase was isolated using a separatory funnel and then purified by fractional vacuum distillation at 2.0 Torr through a short Vigreux column. A total of 33.9 g of desired product, $C_4F_9SO_2N(H)CH_2CH_2OCH_2CH_2OH$, was collected in Fraction #3 at a head temperature of 136.5-143.5° C. The isolated product collected in Fraction #3 was a clear colorless viscous liquid initially, with a purity determined by GC-FID of 99.25%. GC peak assignments were confirmed by GC-MS. This material ultimately crystallized to a low melting solid with a melting point (mp) of 35.7° C.

Tests have shown that Compound III (H-FBS(EE)) is a useful synergist, which, when combined with one or more surfactants of the present invention and dissolved in an organic solvent at an effective concentration, provided improved particle cleaning performance vs. an organic solvent that is free of surfactant or contains one or more surfactants of the present invention but no synergist.

Synthesis 3: $C_4F_9SO_2N(CH_2CH_2OCH_2CH_2OH)_2$
(IV, FBS(EE)2)

$C_4F_9SO_2NH_2$ (295 g, 0.9867 mol) and $ClCH_2CH_2OCH_2CH_2OH$ (491 g, 3.94 mol) were batch charged to a 1000 mL, 3-necked round bottom flask equipped with a Claisen adapter, water cooled condenser, immersion thermocouple probe, mechanical stirrer and heating mantle. After heating mixture to a set point of 90° C., potassium carbonate (300 g, 2.17 mol) was gradually added with stirring over a period of 15 minutes without significant exotherm or precipitate. Reaction temperature was increased to 120° C. and held for 17 hours. The batch temperature was lowered to 90° C. and 1000 g of hot water was added. The contents were split in a separatory funnel to give 622 g of lower fluorochemical phase. The lower phase was returned to the flask and 300 ml of water, 107 g of 86% phosphoric acid, and 53 g of sodium chloride was added and stirred with the batch, and then poured into a separatory funnel. The bottom layer was then split off to give 669 g. The lower phase was stripped at atmospheric pressure until the pot temperature reached 150° C. The batch was then cooled to 90° C., and with good stirring the stripping was continued under vacuum to remove unreacted $ClCH_2CH_2OCH_2CH_2OH$ and $C_4F_9SO_2NH_2$. Stripping was begun at 90° C. and 103 mm Hg to a receiver that was cooled in dry ice/acetone and continued until the vacuum was 0.4 mm Hg and the batch had reached 100° C. The batch was cooled, vacuum was broken and the receiver was emptied. The distillation was then continued at 0.4 mm Hg. Cut 1 distilled at a head temp of 173-181° C. and a pot temp of 189-200° C., and weighed 34 g. Cut 2 distilled at 0.2 mm Hg at a head temperature of 181-182° C. and a pot temperature of 200-203° C. and weighed 118 g. Cut 3 distilled at 0.2 mm at a head temperature of 181-210° C. and a pot temperature of 207-215° C. and weighed 47 g.

NMR and GC/MS showed cut 2 to be 89.5% the desired $C_4F_9SO_2N(CH_2CH_2OCH_2CH_2OH)_2$ (including minor branched FC isomers), 9.8% $C_4F_9SO_2NHCH_2CH_2OCH_2CH_2OH$, 0.6% $C_4F_9SO_2NH_2$. GC/MS showed cut 3 to be 83.1% the desired $C_4F_9SO_2N(CH_2CH_2OCH_2CH_2OH)_2$ (including minor branched FC isomers).

When dissolved in an organic solvent at an effective concentration, Compound IV (FBS(EE)2) has been shown to provide improved particle cleaning performance vs. an organic solvent that is free of surfactant.

Synthesis 4: $C_4F_9SO_2N(CH_2CH_2OCH_2CH_2OH)(CH_2CH_2OH)$ (V, FBSE(EE))

$C_4F_9SO_2NHCH_2CH_2OH$ (249 g, 0.725 mol; prepared according to U.S. Pat. No. 7,169,323) and $ClCH_2CH_2OCH_2CH_2OH$ (211 g, 1.70 mol) were batch charged to a 1000 mL, 3-necked round bottom flask equipped with a Claisen adapter, water cooled condenser, immersion thermocouple probe, mechanical stirrer and heating mantle. After heating mixture to a set point of 90° C., potassium carbonate (120 g, 0.86 mol) was gradually added with stirring over a period of 15 minutes without significant exotherm or precipitate. Reaction temperature was increased to 120° C. and held for 17 hours. GC-FID analysis (in acetone) revealed the presence of about 37% unreacted $ClCH_2CH_2OCH_2CH_2OH$, no detectible $C_4F_9SO_2NHCH_2CH_2OH$, and 58.3% $C_4F_9SO_2N(CH_2CH_2OCH_2CH_2OH)(CH_2CH_2OH)$. The batch temperature was lowered to 90° C. and 230 g of hot water was added. After addition of water 18 g of 85% phosphoric acid was added to the batch. The contents were phase split in a reparatory funnel to give 385 g of lower fluorochemical phase. The lower phase was returned to the flask and 100 ml of water, and 40 g of 86% phosphoric acid, were added and stirred with the batch. After sitting for an hour, no phase split could be seen. 377 g of methyl t-butyl ether was added to the batch, which was allowed to stir for 15 min. After the phase split, 759 g of methyl t-butyl ether product solution was separated from 166 g of lower aqueous phase. The ether solution was stripped at atmospheric pressure until the batch temperature reached 77° C. The batch was further stripped at 8.6 mm Hg until the pot temperature reached 132° C., and then the receiver was emptied. Then stripping was continued until the pressure reached 2.2 mm Hg at a head temperature of 171° C. The receiver was then emptied and collection of the product cut was begun at 0.2 mm Hg vacuum and a head temperature of 172° C. and a pot temperature of 184° C. Distillation was continued until the pot reached 195° C. to give 183 g of distillate. GC-FID analysis of the distillate showed the material to be 95.4% desired product (V). At room temperature the material crystallized to a low melting solid with a melting point of 45.1° C. as determined by DSC.

When dissolved in an organic solvent at an effective concentration, Compound V (FBSE(EE)) has been shown to provide improved particle cleaning performance vs. an organic solvent that is free of surfactant.

Synthesis 5: $C_4F_9SO_2NH(CH_2CH_2OCH_2CH_2OCH_2CH_2OH)$ (VI, H-FBS (EEE)) and $C_4F_9SO_2N(CH_2CH_2OCH_2CH_2OCH_2CH_2OH)_2$ (VII, FBS (EEE)2)

$C_4F_9SO_2NH_2$ (640 g, 2.14 mol) and $ClCH_2CH_2OCH_2CH_2OCH_2CH_2OH$ (288 g, 1.71 mol, available from Aldrich, St. Louis, Mo.) were batch charged to a 2000 mL, 3-necked round bottom flask equipped with a Claisen adapter, water cooled condenser, immersion thermocouple probe, mechanical stirrer and heating mantle. After heating mixture to a set point of 90° C., sodium carbonate (189 g, 1.81 mol) was gradually added with stirring over a period of 15 minutes without significant exotherm or precipitate. Reaction temperature was increased to 120° C. and held for 17 hours. The batch temperature was lowered to 90° C. and 750 g of hot water was added followed by 103 g of 85% phosphoric acid. The contents were phase split in a separatory funnel. The lower fluorochemical phase was returned to the flask and 508 ml of water, 53 g of 86% phosphoric acid, and 53 g of sodium chloride were added and stirred with the batch, and then poured back into a separatory funnel. The bottom layer was then phase split off to give 888 g of crude product. An aliquot of the washed crude was removed and analyzed by GC-FID in acetone revealing the presence of about 22% unreacted $C_4F_9SO_2NH_2$, 60% $C_4F_9SO_2NH(CH_2CH_2OCH_2CH_2OCH_2CH_2OH)$ and 21% $C_4F_9SO_2N(CH_2CH_2OCH_2CH_2OCH_2CH_2OH)_2$. The crude product mixture was stripped at atmospheric pressure until the pot temperature reached 150° C. The batch was then cooled to 90° C., and with good stirring the stripping was continued under vacuum to remove unreacted $ClCH_2CH_2OCH_2CH_2OCH_2CH_2OH$ and $C_4F_9SO_2NH_2$. Stripping was begun at 90° C. and 103 mm Hg to a receiver that was cooled in dry ice/acetone and continued until the pressure dropped to 0.4 mm Hg and the batch had reached 100° C. The batch was cooled, vacuum was broken and the receiver was emptied. The distillation was then continued at 0.4 mm Hg pressure. Cut 1 distilled at a head temp of 136-158° C. and a pot temp of 163-174° C. Cut 2 distilled at 0.2 mm Hg at a head temperature of 140-180° C. and a pot temperature of 174-195° C. and weighed 282 g. Cut 3 distilled at 0.2 mm Hg at a head temperature of 181-193° C. and a pot temperature of 193-215° C. and weighed 69 g. GC-FID analysis of Cut 2 revealed the presence of 97.2% $C_4F_9SO_2NH(CH_2CH_2OCH_2CH_2OCH_2CH_2OH)$ (VI) and 2.8% $C_4F_9SO_2N(CH_2CH_2OCH_2CH_2OCH_2CH_2OH)_2$ (VII), and was a white solid at room temperature with a melting point of 58.5° C. GC-FID analysis of Cut 3 revealed the presence of 66% $C_4F_9SO_2NH(CH_2CH_2OCH_2CH_2OCH_2CH_2OH)$ (VI) and 33.3% $C_4F_9SO_2N(CH_2CH_2OCH_2CH_2OCH_2CH_2OH)_2$ (VII). Cut 3 was a thick yellow liquid at room temperature. The chemical structure of the major product collected in cut 2 was confirmed to be (VI) by $^1H$ and $^{19}F$ NMR analysis.

When dissolved in an organic solvent at an effective concentration, compound VII (FBS(EEE)2 is expected to provide improved particle cleaning performance vs. an organic solvent that is free of surfactant. Compound VI (H-FBS(EEE)) is expected to be a useful synergist, which, when combined with compound VII or one or more other surfactants of the present invention and dissolved in an organic solvent at an effective concentration, will provide improved particle cleaning performance vs. an organic solvent that is free of surfactant or contains one or more surfactants of the present invention but no synergist.

Synthesis 6: $C_4F_9SO_2N(CH_2CH_2OH)CH_2CH(CH_3)OH$ (VIII, FBSEP)

$C_4F_9SO_2NHCH_2CH_2OH$ (500.00 g, 1.43 mol, H-FBSE), $K_2CO_3$ powder (53 g, 0.39 mol), and anhydrous propylene carbonate (500 g, 4.9 mol) were batch charged to a 1.0 L round bottom 3-necked flask equipped with a Claisen adapter, water cooled condenser with nitrogen inlet line, immersion thermocouple probe, overhead stirrer and heating mantle. The reaction mixture was gradually heated to 130° C. It was heated and stirred overnight. After cooling to 84° C., an aliquot of the reaction mixture was removed and analyzed by GC in acetone. GC-FID analysis revealed the presence of about 56 area % unreacted propylene carbonate, 2.65% $C_4F_9SO_2N(H)CH_2CH_2OH$ and 32.6% $C_4F_9SO_2NCH_2CH_2OH$ [$CH_2CH(CH_3)OH$]. At 84° C., 800 ml of water was added to the batch followed by slow addition of 100 g of 85% phosphoric acid. The batch was phase split in a separatory funnel to give 884 g of lower crude fluorochemical product. The lower phase was washed with 500 g of water with 10 g of NaCl dissolved in it to give 773 g of lower fluorochemical layer. The fluorochemical phase was stripped at atmospheric pressure until the pot temperature reached 100° C., giving 160 g of distillate. A precut was collected by distilling under vacuum (57 to 2 mm Hg) when the pot temperature was 35-143° C. A second precut was distilled at 2 to 1.4 mm Hg with a pot temperature of 143-183° C. and a head temperature of 105-152° C., resulting in the collection of 62 g of distillate. GC analysis of this second precut by GC-FID showed it to be 11.3 area % H-FBSE and 72% the desired product (VIII). The main product cut was distilled at 1.4 to 0.2 mm Hg at a pot temp of 183-215° C. and a head temperature of 150-160° C., yielding 308 g of distillate. GC analysis showed this material to be 70.6% desired product (VIII). Recrystallization of the distilled main cut from toluene led to material that was 98.4% desired product (VIII) by GC-FID.

When dissolved in an organic solvent at an effective concentration, compound VIII (FBSEP) is expected to provide improved particle cleaning performance vs. an organic solvent that is free of surfactant.

Synthesis 7: $C_4F_9SO_2N(CH_2CH_2OH)_2$ (IX, FBSEE)

$C_4F_9SO_2N(CH_2CH_2OH)_2$ was prepared as described in US Patent application US 2010/0160458, page 3, [0058].

When dissolved in an organic solvent at an effective concentration, Compound IX (FBSEE) has been shown to provide improved particle cleaning performance vs. an organic solvent that is free of surfactant.

Synthesis 8: $C_4F_9SO_2NH(CH_2CH_2OH)$ (X, H-FBSE)

$C_4F_9SO_2NH(CH_2CH_2OH)$ was prepared as described in U.S. Pat. No. 6,890,452, column 9 line 50-column 10 line 17.

Tests have shown that Compound X (H-FBSE) is a useful synergist, which, when combined with one or more surfactants of the present invention and dissolved in an organic solvent at an effective concentration, provides improved particle cleaning performance vs. an organic solvent that is free of surfactant or contains one or more surfactants of the present invention but no synergist.

Synthesis 9: $C_4F_9SO_2N(CH_3)(CH_2CH_2O)_7CH_3$ (XI, FC-4171)

$C_4F_9SO_2N(CH_3)(CH_2CH_2O)_7CH_3$ was prepared as described in U.S. Pat. No. 7,662,896, Column 21, lines 15-51.

Examples (EX) 1-21 and Comparative Examples (CE) 1-17: Surfactant Solubility

A series of $C_4F_9SO_2N$-based fluorochemical surfactants were examined to determine their solubility in various hydrofluoro ether (HFE) solvents, including four segregated HFEs (Novec 7100, 7200, 7300, and 7500 available from 3M Company, St Paul, Minn.), one non-segregated HFE (PF-7600 available from 3M Company), and one HFE-Alcohol blend (Novec 71IPA available from 3M Company). Solubility was determined by preparing mixtures of each surfactant in the solvent at various concentrations and determining solubility at each concentration by visual inspection based on the clarity of the solutions after thorough mixing at room temperature. Surfactants that were not completely soluble at a given concentration produced hazy mixtures, whereas surfactants that were completely soluble at a given concentration produced clear homogeneous solutions with no haze. The highest concentration of each surfactant to give a clear, homogeneous solution in each HFE solvent (expressed as wt % surfactant dissolved in HFE solvent) was taken as the maximum solubility. The results of the solubility determinations are summarized in Table 1, below.

TABLE 1

Surfactant Solubility at Room Temperature (23° C.)

| EX#/CE# | Surfactant | Solvent | Max. Solubility (wt %) |
|---|---|---|---|
| CE 1 | H-FBSE (X) | Novec 7100 | 0.21 |
| CE 2 | H-FBSE (X) | Novec 7200 | 0.16 |
| CE 3 | H-FBSE (X) | Novec 7300 | 0.06 |
| CE 4 | H-FBSE (X) | PF-7600 | 1.5 |
| CE 5 | H-FBSE (X) | Novec 71IPA | >10 |
| CE 6 | H-FBS(EE) (III) | Novec 7100 | >10 |
| CE 7 | H-FBS(EE) (III) | Novec 7200 | >10 |
| CE 8 | H-FBS(EE) (III) | Novec 7300 | >10 |
| CE 9 | H-FBS(EE) (III) | Novec 7500 | >10 |
| CE 10 | H-FBS(EE) (III) | PF-7600 | >10 |
| CE 11 | H-FBS(EE) (III) | Novec 71IPA | >10 |
| CE 12 | FC-4171 (XI) | Novec 7100 | >10 |
| CE 13 | FC-4171 (XI) | Novec 7200 | >10 |
| CE 14 | FC-4171 (XI) | Novec 7300 | 0.5 |
| CE 15 | FC-4171 (XI) | Novec 7500 | 0.1 |

TABLE 1-continued

Surfactant Solubility at Room Temperature (23° C.)

| EX#/CE# | Surfactant | Solvent | Max. Solubility (wt %) |
|---|---|---|---|
| CE 16 | FC-4171 (XI) | PF-7600 | >10 |
| CE 17 | FC-4171 (XI) | Novec 71IPA | >10 |
| EX 1 | FBSEE (IX) | Novec 7100 | 0.06 |
| EX 2 | FBSEE (IX) | Novec 7200 | 0.04 |
| EX 3 | FBSEE (IX) | Novec 7300 | 0.03 |
| EX 4 | FBSEE (IX) | PF-7600 | 0.6 |
| EX 5 | FBSEE (IX) | Novec 71IPA | 8.1 |
| EX 6 | FBSE(EE) (V) | Novec 7100 | 1.5 |
| EX 7 | FBSE(EE) (V) | Novec 7200 | 0.8 |
| EX 8 | FBSE(EE) (V) | Novec 7300 | 0.9 |
| EX 9 | FBSE(EE) (V) | Novec 7500 | 0.2 |
| EX 10 | FBSE(EE) (V) | PF-7600 | >10 |
| EX 11 | FBSE(EE) (V) | Novec 71IPA | >10 |
| EX 12 | FBS(EE)2 (IV) | Novec 7100 | >10 |
| EX 13 | FBS(EE)2 (IV) | Novec 7200 | 0.2-0.5 |
| EX 14 | FBS(EE)2 (IV) | Novec 7300 | 0.2-0.3 |
| EX 15 | FBS(EE)2 (IV) | Novec 7500 | 0.2 |
| EX 16 | FBS(EE)2 (IV) | PF-7600 | 8-9 |
| EX 17 | FBS(EE)2 (IV) | Novec 71IPA | >10 |
| EX 18 | FBSEP (VIII) | Novec 7100 | 4.0 |
| EX 19 | FBSEP (VIII) | Novec 7300 | 1.4 |
| EX 20 | FBSEP (VIII) | PF-7600 | >10 |
| EX 21 | FBSEP (VIII) | Novec 71IPA | >10 |

In general, all of the $C_4F_9SO_2N$-based fluorochemical surfactants tested showed good solubility (>0.025% or >250 ppm) in all the HFE solvents. Surfactants containing at least one oligomeric ethylene oxide unit bound to nitrogen center (e.g., Structure 1, where n or x is >1) generally showed improved solubility in HFE solvents. Similarly, surfactants containing at least one methyl branched alkylene oxide unit (e.g., Structure 1 where $R_1$ or $R_2$ is a methyl group as in FBSEP (VIII)) also showed improved solubility in HFE solvents. In general, the surfactants showed the highest solubility in the non-segregated HFE, PF-7600, and in the HFE-Alcohol blend, Novec 71IPA. In a number of cases, the solubility of the $C_4F_9SO_2N$-based fluorochemical surfactants in the HFE solvent was surprisingly high (>0.10% or >1000 ppm).

Examples 22-30 and Comparative Examples 18-24: Cleaning Performance

A study was conducted using Novec 7100 and Novec 71IPA base solvents with and without the soluble surfactants identified above to determine the impact of dissolved surfactant on cleaning performance of the fluids. In some cases a single surfactant was employed. In other cases a mixture of two surfactants was employed. In all cases the total concentration of fluorochemical surfactant employed was 0.20 wt % (or 2000 ppm) in the base fluid. Cleaning results were compared to pure Novec fluid controls containing no surfactant. The cleaning trials were performed on heavily soiled CMOS sensors containing a high pixel density. These sensors are known to be extremely difficult to clean such that they are essentially free of (particle contaminants.

A precision solvent cleaning system (SK-04Y-6008 customized cleaning system from YMPT, Thailand) was used to clean the CMOS sensors using the process outlined below.

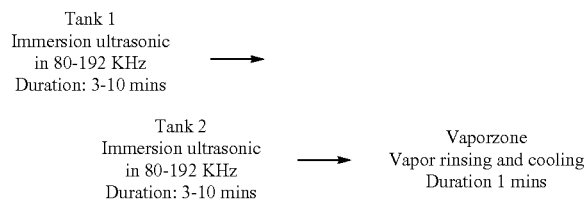

The cleaning performance of each cleaning fluid composition was judged based on the percentage of particles originally present on the CMOS surface that were removed by the cleaning fluid after completion of the cleaning process. The percentage of particles removed was determined by optical microscopy inspection of the CMOS sensors before and after cleaning.

The original (heavily soiled) CMOS sensor was first inspected using an optical microscope and a series of Pre-Clean images were recorded. The CMOS sensor was then cleaned in the precision cleaning system using the process described above and the proscribed solvent/surfactant combination. After cleaning, the CMOS sensor was inspected again by optical microscopy and a Post-Clean image recorded to determine particle counts remaining on the sensor. In this way, the % removal of particles after cleaning of CMOS sensors was determined.

The Novec 71IPA and Novec 7100 based cleaning fluid compositions tested (with and without FC Surfactants) and the cleaning performance (or % particle removal) results obtained with each are summarized in Tables 2 and 3, respectively. The best performing cleaning fluid compositions were able to remove 90-100% of the particles that were originally present on the CMOS surface and these best performing compositions are grouped at the bottom of each Table.

TABLE 2

| | Percent Particle Removal in Novec 71IPA | | | |
|---|---|---|---|---|
| EX#/ CE# | Surfactant Structure | Short Name (Compound #) | % Surfactant Added | % Removal |
| CE 18 | None | Novec 71IPA only (Control) | 0 | 50-80 |
| CE 19 | [structure] | H-FBSE (X) | 0.2 | 50-80 |
| CE 20 | [structure] | H-FBS(EE) (III) | 0.2 | 50-80 |
| EX 22 | [structure] | FBS(EE)2 (IV) | 0.2 | 50-80 |
| CE 21 | [structure] | FC-4171 (XI) | 0.2 | 50-80 |
| EX 23 | [structure] + [structure] | H-FBS(EE) (III) + FBSEE (IX) | 0.1333 0.0667 | 50-80 |

TABLE 2-continued
Percent Particle Removal in Novec 71IPA
| EX#/ CE# | Surfactant Structure | Short Name (Compound #) | % Surfactant Added | % Removal |
|---|---|---|---|---|
| EX 24 | 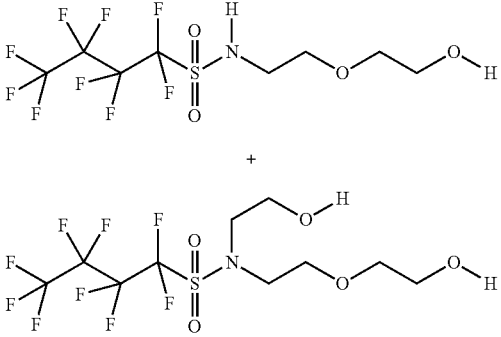 + 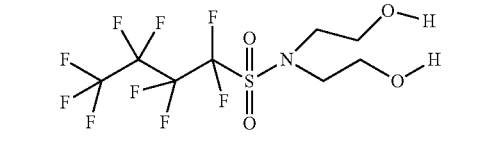 [SMILES: O=S(=O)(N(CCO)CCO)C(F)(F)C(F)(F)C(F)(F)C(F)(F)F] | H-FBS(EE) (III) + FBSE(EE) (V) | 0.1333 0.0667 | 50-80 |
| EX 25 | 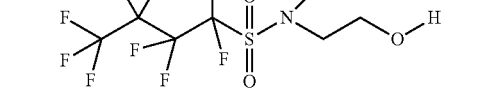 | FBSEE (IX) | 0.2 | 90-100 |
| EX 26 | 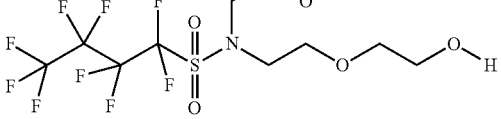 | FBSE(EE) (V) | 0.2 | 90-100 |
| EX 27 | 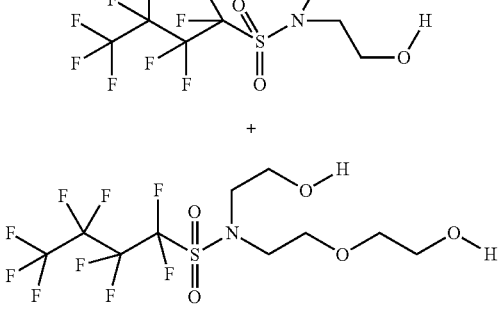 + 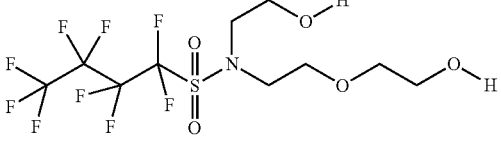 | H-FBSE (X) + FBSE(EE) (V) | 0.1333 0.0667 | 90-100 |
| EX 28 | 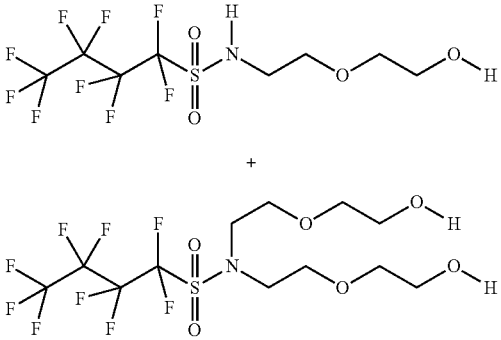 + 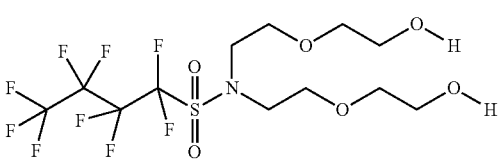 [SMILES: O=S(=O)(N(CCOCCO)CCOCCO)C(F)(F)C(F)(F)C(F)(F)C(F)(F)F] | H-FBS(EE) (III) + FBS(EE)2 (IV) | 0.1333 0.667 | 90-100 |

TABLE 3

Percent Particle Removal in Novec 7100

| EX#/CE# | Surfactant Structure | Short Name (Compound #) | % Surfactant Added | % Removal |
|---|---|---|---|---|
| CE 22 | None | Novec 7100 only (Control) | 0 | 50-80 |
| CE 23 | [structure] | H-FBS(EE) (III) | 0.2 | 50-80 |
| EX 29 | [structure] | FBS(EE)2 (IV) | 0.2 | 50-80 |
| CE 24 | [structure] | FC-4171 (XI) | 0.2 | 50-80 |
| EX 30 | [structure] | FBSE(EE) (V) | 0.2 | 90-100 |

Combinations of Novec HFE base fluids with certain $C_4F_9SO_2N$-based fluorochemical surfactants or surfactant mixtures provide superior particle cleaning performance when compared to the base Novec fluids alone (Control fluids with no surfactant). The results further indicate that non-ionic $C_4F_9SO_2N$-based fluorochemical surfactants according to Structure (1), including FBSEE (IX), FBSE (EE) (V), and FBS(EE)2 (IV) provide both adequate solubility in the Novec fluids and the best cleaning performance. Other nonionic $C_4F_9SO_2N$-based fluorochemical surfactants with different structural motifs, like FC-4171 (XI), and ionic (or protic) $C_4F_9SO_2N$-based fluorochemical surfactants, like H-FBSE (X) and H-FBS(EE) (III) are less effective in terms of particle removal efficiency. Surprisingly, in some cases, combining a nonionic $C_4F_9SO_2N$-based fluorochemical surfactant, like FBS(EE)2 (IV), with an ionic (or protic) $C_4F_9SO_2N$-based fluorochemical surfactant, like H-FBS (EE) (III), as in Example 28, can produce better cleaning performance than either the nonionic surfactant or the ionic surfactant alone.

The nonionic $C_4F_9SO_2N$-based fluorochemical surfactants of the present disclosure have been shown to be highly effective at improving the particle cleaning performance of HFE based cleaning fluids such as Novec 7100 and Novec 71IPA. Furthermore, these new surfactant-containing cleaning formulations have been shown to be useful in cleaning heavily soiled CMOS sensors.

Examples 31-32 and Comparative Examples 25-29: Particle Reattachment Performance According to theory, particle cleaning performance depends on two processes: (1) particle removal, (2) particle re-attachment. Process (2) is believed to be critical to overall cleaning performance. Therefore, the following experiment was designed to measure the particle reattachment performance of two pure Novec fluids (Novec 7100 and Novec 71IPA) in comparison to the performance of Novec 7100 with added fluorochemical surfactant. A total of five surfactants (H-FBSE (X), H-FBS(EE) (III), FBSE(EE) (V), FBS (EE)2 (IV), and FC-4171 (XI)) were tested in Novec 7100 at a concentration of 0.10% (1000 ppm), to determine how the presence (or absence) of surfactant, as well as surfactant structure, impacts particle reattachment performance.

Surfactant solutions in Novec 7100 were prepared by mixing each surfactant into Novec 7100 at a concentration of 1000 ppm until all the surfactant was dissolved. Then, PSL particles (Polystyrene Latex test particles made by Moritex, DC-05, with a warranted average particle diameter is 5.0 μm±0.4 μm) were mixed (concentration: 0.008 g particles/kg fluid) into each sample of Novec 7100 to create a particle dispersion in the fluid. Similar particle dispersions in pure Novec 7100 and Novec 71IPA (with no surfactant) were prepared as controls. A pre-cleaned bare silicon wafer (4 inch diameter) was then dipped into each fluid mixture (containing the PSL particle dispersion) allowing 3 seconds to immerse each wafer, followed by a 3 second hold at full immersion, and 4 seconds to remove each wafer, while stirring each dispersion at 150-170 rpm. Next, each wafer was rinsed with the base Novec fluid vapor (2 min) and air dried (30 sec) under ambient conditions. Finally, the total particle count (number of attached particles on each wafer) was measured using a wafer surface analyzer (WM-7S, made by TOPCON). The results are summarized in Table 4.

TABLE 4

Total Particle Counts (Number of particles/wafer) after Immersion in PSL Dispersion and Vapor Rinsing

| EX#/CE# | Surfactant Structure | Short Name (Compound #) | HFE Solvent | Total Particle Count |
|---|---|---|---|---|
| CE 25 | None | None | Novec 7100 Only (Control) | 1045 |
| CE 26 | None | None | Novec 71IPA Only (Control) | 519 |
| CE 27 | (structure) | H-FBS(EE) (III) | Novec 7100 | 795 |
| CE 28 | (structure) | H-FBSE (X) | Novec 7100 | 899 |
| EX 31 | (structure) | FBS(EE)2 (IV) | Novec 7100 | 364 |
| CE 29 | (structure) | FC-4171 (XI) | Novec 7100 | 553 |
| EX 32 | (structure) | FBSE(EE) (V) | Novec 7100 | 458 |

These results clearly show that all of the surfactants tested improve the particle reattachment performance of Novec 7100 when employed at a concentration of 1000 ppm, as evidenced by the relatively lower final particle counts when surfactant was present. However, only a few surfactants provide performance superior to the present industry benchmark, Novec 71IPA. These include the two nonionic surfactants, FBSE(EE) (V) and FBS(EE)2 (IV). The other nonionic surfactant, FC-4171 (XI), and the two ionic (or protic) surfactants, H-FBSE (X) and H-FBS(EE) (III), did not perform as well in this particle reattachment test. Thus, this experiment indicates that FBSE(EE) (V) and FBS(EE)2 (IV) are particularly and surprisingly effective at inhibiting particle reattachment in Novec cleaning fluids and thereby improving particle cleaning performance.

Other embodiments of the invention are within the scope of the appended claims.

What is claimed is:

1. A composition comprising:
a fluorinated or perfluorinated organic solvent; and
a fluorinated surfactant of the general formula (1):

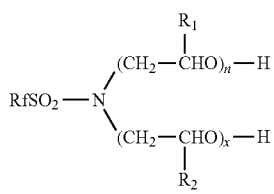

where Rf is a perfluoroalkyl group having 1-6 carbon atoms; each occurrence of $R_1$ and $R_2$ is independently H or $CH_3$; n is 1-3; and x is 1-3.

2. The composition according to claim 1, wherein the fluorinated surfactant is present in the composition in an amount of between 0.01 and 1 wt. % based on the total weight of the composition.

3. The composition according to claim 1, wherein the organic solvent comprises a non-flammable fluorinated or perfluorinated organic solvent.

4. The composition according to claim 1, wherein the fluorinated or perfluorinated organic solvent comprises a primary organic solvent that is present in the composition at greater than 50 wt. % based on the total weight of the composition, and wherein the primary organic solvent comprises a hydrofluoroether, hydrofluorocarbon, hydrofluoroolefin, hydrochlorofluoroolefin, fluoroketone, perfluoroketone, or combinations thereof.

5. The composition according to claim 4, wherein the primary organic solvent comprises a hydrofluoroether.

6. The composition according to claim 5, wherein the primary organic solvent comprises a segregated hydrofluoroether.

7. The composition according to claim 1, wherein the fluorinated or perfluorinated organic solvent is present in the composition in an amount of at least 95 wt. %, based on the total weight of the composition.

8. The composition according to claim 1, further comprising a co-solvent.

9. The composition according to claim 8, wherein the co-solvent comprises an alcohol.

10. The composition according to claim 9, wherein the co-solvent is present in the composition in an amount of between 1 and 10 wt. %, based on the total weight of the composition.

11. The composition according to claim 1, further comprising a second fluorinated surfactant according to general formula (2):

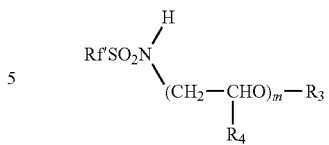

where m is 1-3, each occurrence of $R_4$ is H or $CH_3$, $R_3$ is H or an alkyl group, and Rf' is a perfluoroalkyl group having 1-6 carbon atoms.

12. The composition according to claim 11, wherein the second surfactant is present in the composition in an amount of between 0.01 and 1 wt. %, based on the total weight of the composition.

13. The composition according to claim 1, wherein, Rf in general formula (1) is a perfluoroalkyl group having 4 carbon atoms and at least one of $R_1$ and $R_2$ is H.

14. A process for removing contaminants from a substrate, the process comprising contacting the substrate with a composition according to claim 1.

* * * * *

UNITED STATES PATENT AND TRADEMARK OFFICE
CERTIFICATE OF CORRECTION

| | | |
|---|---|---|
| PATENT NO. | : 10,017,713 B2 | Page 1 of 1 |
| APPLICATION NO. | : 15/508939 | |
| DATED | : July 10, 2018 | |
| INVENTOR(S) | : Lamanna et al. | |

It is certified that error appears in the above-identified patent and that said Letters Patent is hereby corrected as shown below:

In the Specification

Column 5, Line 15, Delete "thereof such" and insert -- thereof. Such --, therefor.

Column 5, Line 49, Delete "CnF2n-1SO2N-" and insert -- CnF2n+1SO2N- --, therefor.

Column 7, Line 10, Delete "fluxes," and insert -- fluxes; --, therefor.

Column 7-8, Lines 57-67 [Column 7] and 1-9 [Column 8], Delete "C4F9SO2N(H)CH2CH(CH3)OH and 24% C4F9SO2N[CH2CH(CH3)OH]2 (mix of two diastereomers). Peak assignments were confirmed by GC-MS. To the reaction mixture was added 69.4 g of deionized water and 19.4 g of 20 wt% H2S04(aq). After heating to 60° C. to reduce viscosity the reaction mixture was stirred vigorously to neutralize all residual base and then transferred to a separatory funnel and allowed to phase separate. The lower product phase was separated, washed with about 60 mL of additional hot water and then phase separated again. The lower product phase was isolated and then dissolved in 240 g of MTBE (methyl t-butyl ether available from Sigma-Aldrich, St Louis, Mo.) to cut viscosity and facilitate additional extractions. After filtration by gravity through fluted filter paper, 5 the product solution in MTBE was transferred to a 1.0 L separatory funnel and extracted with three 300 mL portions of deionized (DI) water. The upper MTBE/product phase was isolated and then concentrated on a rotary evaporator at 20 Torr., 20-50° C. to remove bulk of MTBE solvent to isolate crude product." and insert the same on Column 7, Line 56 as the continuation of the same paragraph.

Column 10, Line 59, Delete "reparatory" and insert -- separatory --, therefor.

Column 14, Line 64, Delete "(particle" and insert -- particle --, therefor.

Signed and Sealed this
Nineteenth Day of March, 2019

Andrei Iancu
*Director of the United States Patent and Trademark Office*